(12) United States Patent
Sakal et al.

(10) Patent No.: US 7,276,047 B2
(45) Date of Patent: Oct. 2, 2007

(54) DUCTAL LAVAGE MICROCATHETER WITH USER ACTIVATED VALVE AND NITINOL INTRODUCER

(75) Inventors: Robert Sakal, Bolton, MA (US); Meghan Brennan, Newburyport, MA (US); Douglas Macarthur, Acton, MA (US); Ben E. Morris, Louisville, KY (US); Todd A. Hall, Goshen, KY (US); Simon Furnish, New York, NY (US)

(73) Assignee: Cytyc Corporation, Marlborough, MA (US)

( * ) Notice: Subject to any disclaimer, the term of this patent is extended or adjusted under 35 U.S.C. 154(b) by 626 days.

(21) Appl. No.: 10/746,117

(22) Filed: Dec. 23, 2003

(65) Prior Publication Data
US 2005/0137574 A1   Jun. 23, 2005

(51) Int. Cl.
*A61M 5/178* (2006.01)
*A61B 5/00* (2006.01)
*F16K 7/04* (2006.01)

(52) U.S. Cl. ............... 604/167.04; 600/573; 251/7
(58) Field of Classification Search ........... 604/167.03, 604/167.04; 251/7, 10
See application file for complete search history.

(56) References Cited

U.S. PATENT DOCUMENTS

| 4,209,015 | A | * | 6/1980 | Wicks | 604/165.03 |
| 4,243,034 | A | * | 1/1981 | Brandt | 604/167.01 |
| 4,917,668 | A | * | 4/1990 | Haindl | 604/167.03 |
| 6,413,228 | B1 | * | 7/2002 | Hung et al. | 600/562 |

* cited by examiner

*Primary Examiner*—Michael J. Hayes
(74) *Attorney, Agent, or Firm*—Theodore Allen; Mark J. Casey

(57) ABSTRACT

A medical instrument including a ductal access device comprising a low profile, ergonomic manifold hub usable to introduce fluids into a breast duct and collect ductal fluid samples including ductal epithelial cells and clumps of ductal epithelial cells from within a breast duct. The ductal access device also comprises an elongated access catheter having a distal end, one lumen and dimensions which permit introduction of the distal end through a ductal orifice so that a distal end of the catheter may be positioned distal to the ductal sphincter of a human breast. The medical instrument may also include and activate valve and a Nitinol introducer.

9 Claims, 17 Drawing Sheets

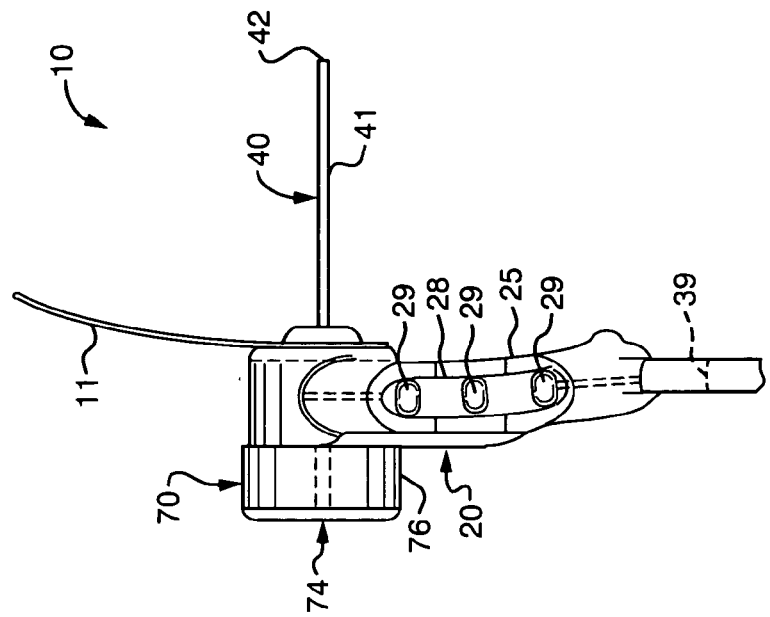
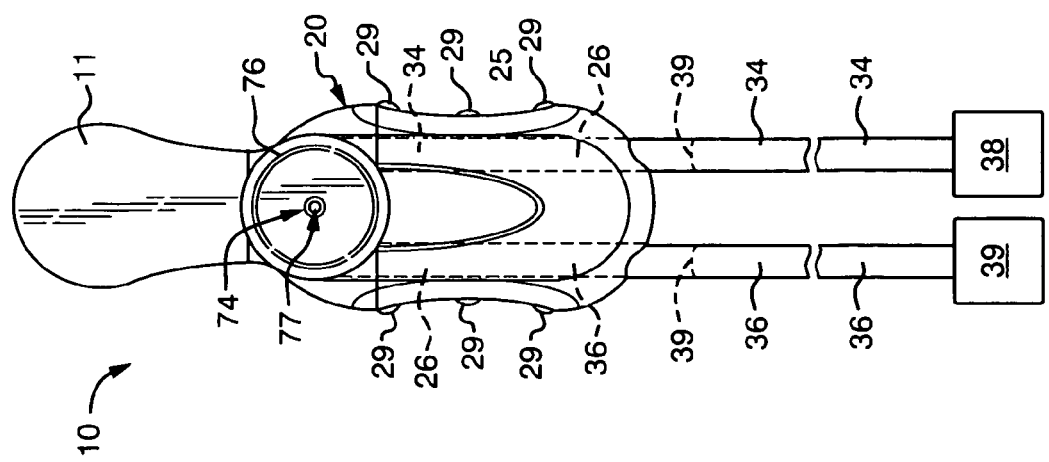

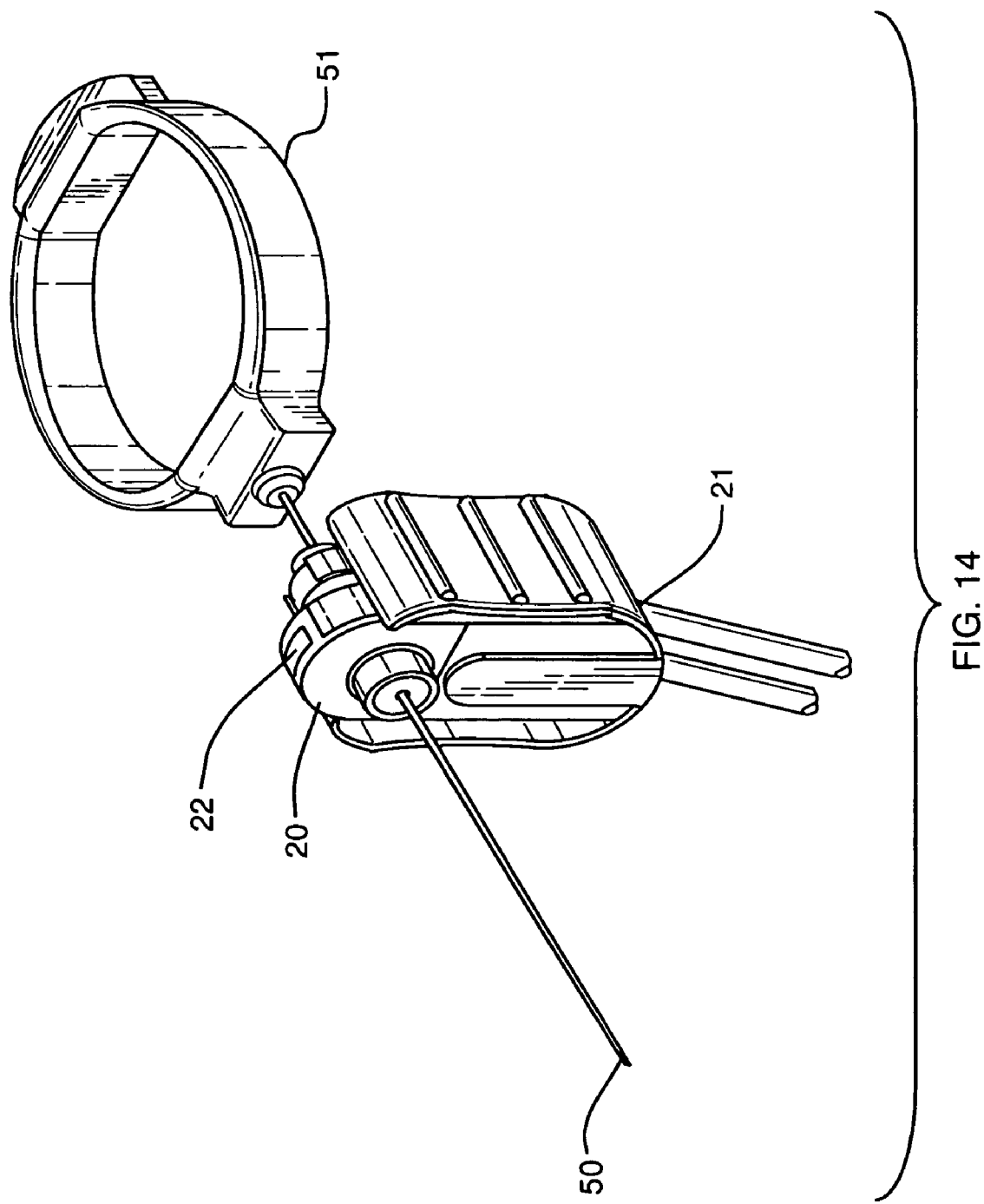

DUCTAL LAVAGE MICROCATHETER WITH USER ACTIVATED VALVE AND NITINOL INTRODUCER

FIELD OF THE INVENTION

The present invention relates to a medical instrument having at least a portion that is introduced into the body of a mammal in order to perform diagnostic or therapeutic medical procedures, more specifically, the present invention relates to a medical instrument useable during a diagnostic or therapeutic medical procedure that is sized for introducing into a breast duct through a ductal orifice.

BACKGROUND OF THE INVENTION

The breast is a specialized, glandular structure including a system of complicated breast ducts that radiate from the nipple and that are bound together by fairly dense connective tissue. Each of these breast ducts includes an associated ductal orifice on the surface of a nipple through which ductal fluid may be expressed. Each duct includes a series of successive interlobular branches that drain through the main, lactiferous branch, which terminates and exits the breast at the nipple via the associated ductal orifice. Immediately proximate the ductal orifice, each lactiferous duct includes a lactiferous sinus in which ductal fluid may accumulate. A ductal sphincter resides within the lactiferous sinus and prevents ductal fluid from unintentionally exiting the breast duct through its associated ductal orifice.

Breast cancer is believed to begin in the lining of these breast ducts. For several decades significant members of the medical community dedicated to studying breast cancer have believed and shown that the cytological analysis of cells retrieved from nipple discharge fluid from within breast ducts may provide valuable information leading to identifying patients at risk for breast cancer. Indeed, Papanicolaou contributed to the genesis of such a possibility of a "Pap" smear for breast cancer by analyzing the cells contained in nipple discharge. More recently, cancer specific markers have been detected in ductal fluid obtained by nipple aspiration. However, the retrieval techniques and instruments used by these members of the medical community did not routinely obtain meaningful ductal fluid samples.

In their attempts to retrieve the breast duct fluid sample including ductal epithelial cells, practitioners introduced wash fluids into a breast duct using indwelling hair-like single lumen catheters. After the fluid was introduced into the duct, the fluid introduction catheters were removed. Then, externally applied nipple aspiration techniques or external pressure applied to the breast were used to collect samples of the ductal fluid. However, these techniques required that significant, sometimes painful, pressure be created on the nipple surface or along the sides of the breast to overcome the fluid retaining properties of the ductal sphincter. Also, these techniques did not routinely provide meaningful ductal fluid samples with a sufficient number of ductal epithelial cells for a meaningful cellular analysis. These techniques typically caused the recovery of samples with twenty or fewer ductal epithelial cells. Additionally, these techniques did not provide samples with cell clusters of 10 or more cells. As a result, the obtained fluid samples could not consistently provide an accurate indication of whether or not the duct from which they were retrieved included precancerous or cancerous cells. Consistent, meaningful ductal epithelial cell samples have been provided by the medical instrument disclosed in U.S. Pat. No. 6,413,228 to Hung et al. that is hereby incorporated by reference in its entirety.

Other medical instruments, such as those used during galactography, are introduced into the breast duct in order to visually determine the presence of cancerous cells within a breast duct. However, these devices typically extend a significant distance out of the breast duct during the performed procedure. These distances may be twelve inches or greater. As a result, when an operator is not holding the tool, the moment created by the weight and length of the section of the instrument extending out of the duct may cause the indwelling portion of the instrument to engage the sidewalls of the duct, torque and/or kink the duct and distort the nipple. These effects on the duct and nipple may impede the procedure by twisting or crimping the indwelling portion of the instrument, possibly injuring the patient's duct and causing significant discomfort to the patient. As a result, a patient must either endure the pain and discomfort caused by these long instruments or an attendant must constantly support the instrument above the patient during the medical procedure.

However, in the confined space around an operating table and in the area surrounding a nipple surface, it is not practical to have an attendant constantly holding the end of the instrument that is extending into the breast duct. Therefore, prior to receiving the procedure, a patient must decide to either experience discomfort during the procedure or choose not to have the procedure performed. Prior art instruments are also not ergonomically designed for easy grasping and adjusting by a practitioner or attendant while acting in the area surrounding a nipple.

SUMMARY OF THE INVENTION

In accordance with one aspect of the present invention, a device for being introduced and positioned within a breast duct for introducing or removing material within the breast duct is provided. The apparatus comprises a manifold hub comprising a sealing fitting for sealing about a ductal introducer extending through the manifold hub at one end of the manifold hub the sealing fitting including an aperture that may be repeatedly opened and closed, the sides of the manifold hub comprising two opposing flexible arms connected at one end to the base of the hub and unconnected at the other end and substantially parallel to one another, the arms are held in a sprung position such that the unconnected ends of said arms compress the sealing fitting such that the aperture is closed and when the arms are compressed, the unconnected ends of the arms no longer compress the sealing fitting and the aperture is opened. The sealing fitting may be comprised of a silicone gasket. The apparatus may also include springs that are located between said flexible arms and the body of said hub such that the springs keep said arms in actuated position. The free ends of the arms may be interlocking hooks. The ductal introducer may be a ring shaped handle. The ductal introducer may be made of a flexible material such as Nitinol and may have a distal tip that tapers from approximately 0.025 inches to approximately 0.008 inches.

In yet another aspect of the present invention, a method for obtaining cellular material from a human breast milk duct is provided. The method may include using a device comprising a manifold hub comprising a fitting for sealing about a ductal introducer extending through said manifold hub at one end of said manifold hub said fitting including an aperture that may be repeatedly opened and closed, the sides of said manifold hub comprising two opposing flexible arms connected at one end to the base of said hub and unconnected at the other end and substantially parallel to one another, said arms are held in a sprung position such that said unconnected ends of said arms compress said fitting such that said aperture is closed and when said arms are compressed, said unconnected ends of said arms no longer compress said fitting and said aperture is opened; and including the steps of inserting the introducer into the internal passageway of a breast duct; and advancing the catheter into the breast duct.

In still yet another aspect of the present invention, a method for obtaining cellular material from a human breast milk duct is provided. The method may include using a device comprising a manifold hub comprising a fitting for sealing about a ductal introducer extending through said manifold hub at one end of said manifold hub said fitting including an aperture that may be repeatedly opened and closed, the sides of said manifold hub comprising two opposing flexible arms connected at one end to the base of said hub and unconnected at the other end and substantially parallel to one another, said arms are held in a sprung position such that said unconnected ends of said arms compress said fitting such that said aperture is closed and when said arms are compressed, said unconnected ends of said arms no longer compress said fitting and said aperture is opened; and including the steps of inserting the introducer into the internal passageway of a breast duct advancing a sheath into the breast duct; and advancing the catheter into the breast duct.

BRIEF DESCRIPTION OF THE FIGURES

FIG. 4 is a top view of the medical instrument of FIG. 1 with infusion and collection lines extending between a manifold hub and respective infusion and collection devices;

FIG. 5 is a side view of the medical instrument illustrated in FIG. 1 carrying infusion and collection lines;

FIGS. 14–17 illustrate an alternative embodiment of the medical instrument according to aspects of the present invention including a ductal lavage microcatheter with user activated valve and Nitinol introducer with a ring shaped handle.

DETAILED DESCRIPTION OF THE INVENTION

Figure 1:
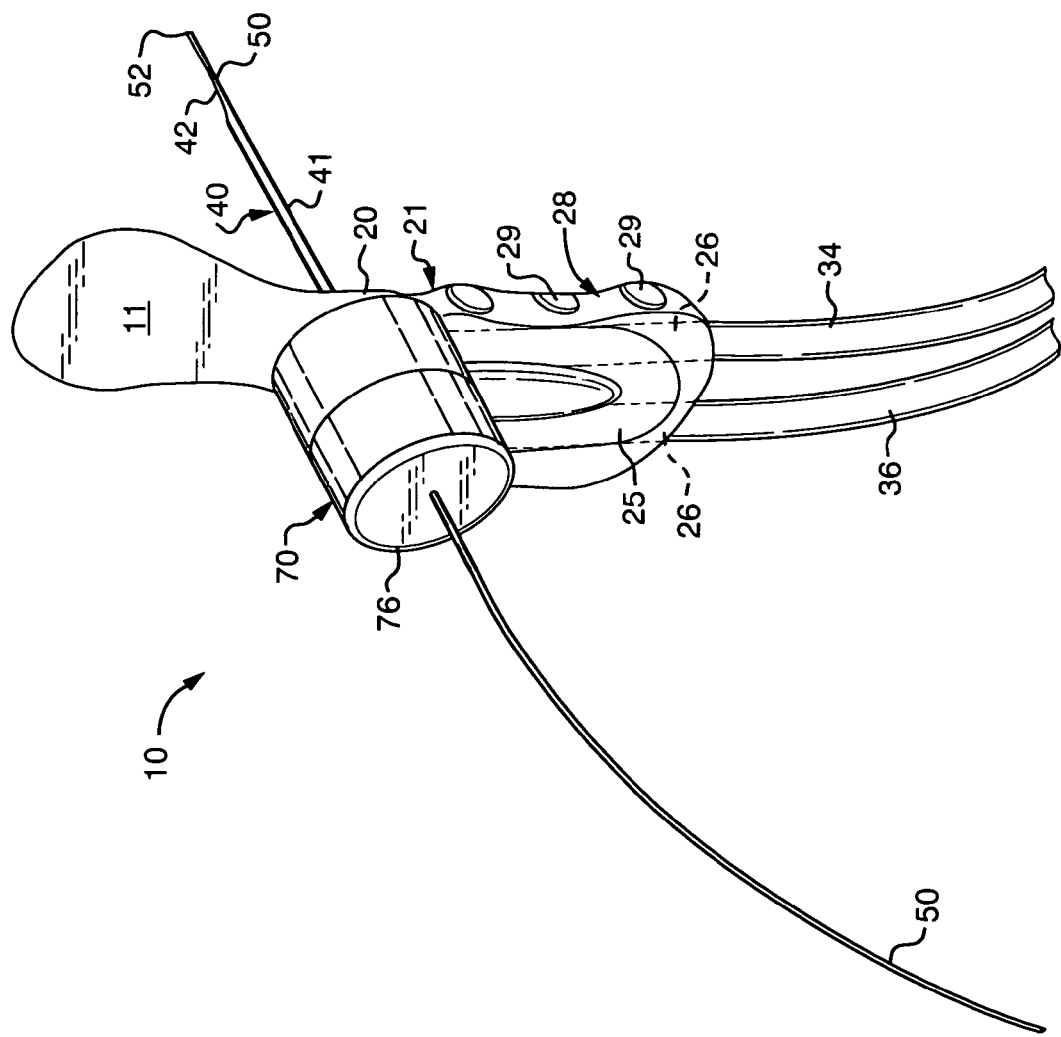
FIG. 1 is a perspective view of a medical instrument according to aspects of the present invention.

FIG. 1 illustrates an embodiment of a low profile, single lumen medical instrument 10 for performing a medical procedure within a breast duct. As used herein, the phrase "medical procedure" may include preparatory procedures, diagnostic procedures or therapeutic procedures. These procedures could include the steps of delivering material(s) into the breast duct and/or retrieving material(s) from within the breast duct.

In an embodiment, the medical instrument 10 may be used to infuse ductal wash fluid delivered to the manifold hub 20 into the breast duct, and collect or draw up ductal fluid samples, including hundreds of ductal epithelial cells and/or cell clusters of greater than ten cells, from within the breast duct for analysis. In another embodiment, the medical instrument 10 may be used to infuse a diagnostic agent or therapeutic agent into a breast duct. As shown in FIGS. 1–8, the instrument 10 may also include a member 11 for securing the instrument 10 to a patient. The securing member 11 may have a biocompatible adhesive on one side for contacting and attaching the instrument 10 to the patient. The member 11 is sized to prevent movement of the manifold hub 20 relative to the body of the patient. In an embodiment illustrated in FIGS. 7 and 8, sections 11A and 11B of the member 11 may be folded onto each other so that the size of the securing member 11 may be adjusted to the patient and the forces created during the procedure. Additionally, the member 11 may be positioned distal a spacer 90 (discussed below).

As illustrated in FIGS. 1–6, the medical instrument 10 includes a manifold hub 20 and a ductal access catheter 40 that extends from a distal end 21 of the manifold hub 20. The access catheter 40 is sized to accesses the breast duct. As illustrated, the manifold hub 20 may have a low profile (height) in a direction that extends parallel to the length of the catheter 40. As illustrated in FIGS. 1–6, the height of the manifold hub 20 may be less than its length (the direction it extends perpendicular to the length of the catheter 40). In a first embodiment, the manifold hub 20 may have a width in a range from about 0.25 inch to about 0.375 inch and a height in a range from about 0.75 inch to about 1.0 inch. In another embodiment, the manifold hub 20 has an internal fluid capacity of 1 ml or less. The low profile of the manifold hub 20 will help to prevent a pivot point from being formed at a location along the length of the catheter 40 at which a large torque may be applied to the duct of a patient during a medical procedure. By eliminating or, at least, significantly reducing any torquing of the duct, the duct will not be kinked, closed due to a change in the position of ductal tissue or injured due to the catheter 40 pushing against the epithelial lining of the duct. The instrument 10 also has an ergonomic design that allows easily handling and grasping by an attendant or practitioner so that the manifold hub 20 and catheter 40 may be easily manipulated.

Figure 7:
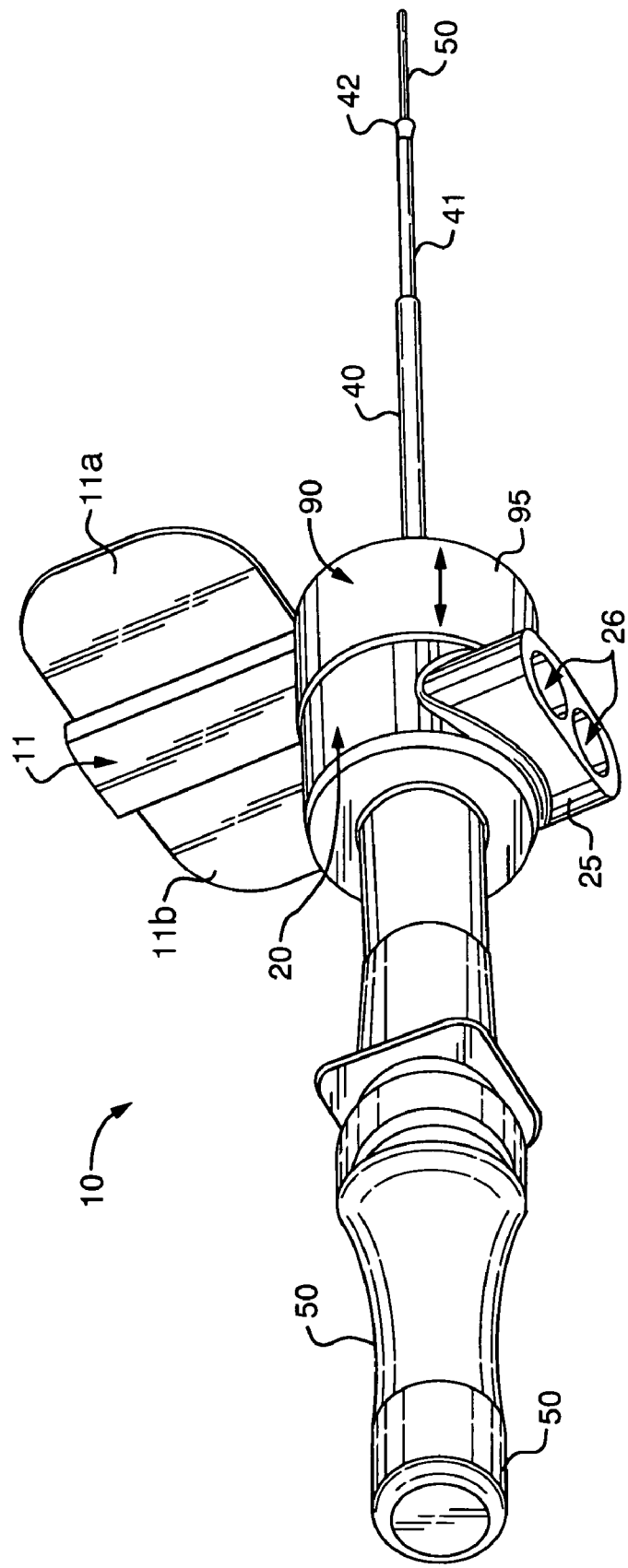
FIGS. 7 and 8 illustrate an alternative embodiment of the medical instrument according to aspects of the present invention.
Figure 8:
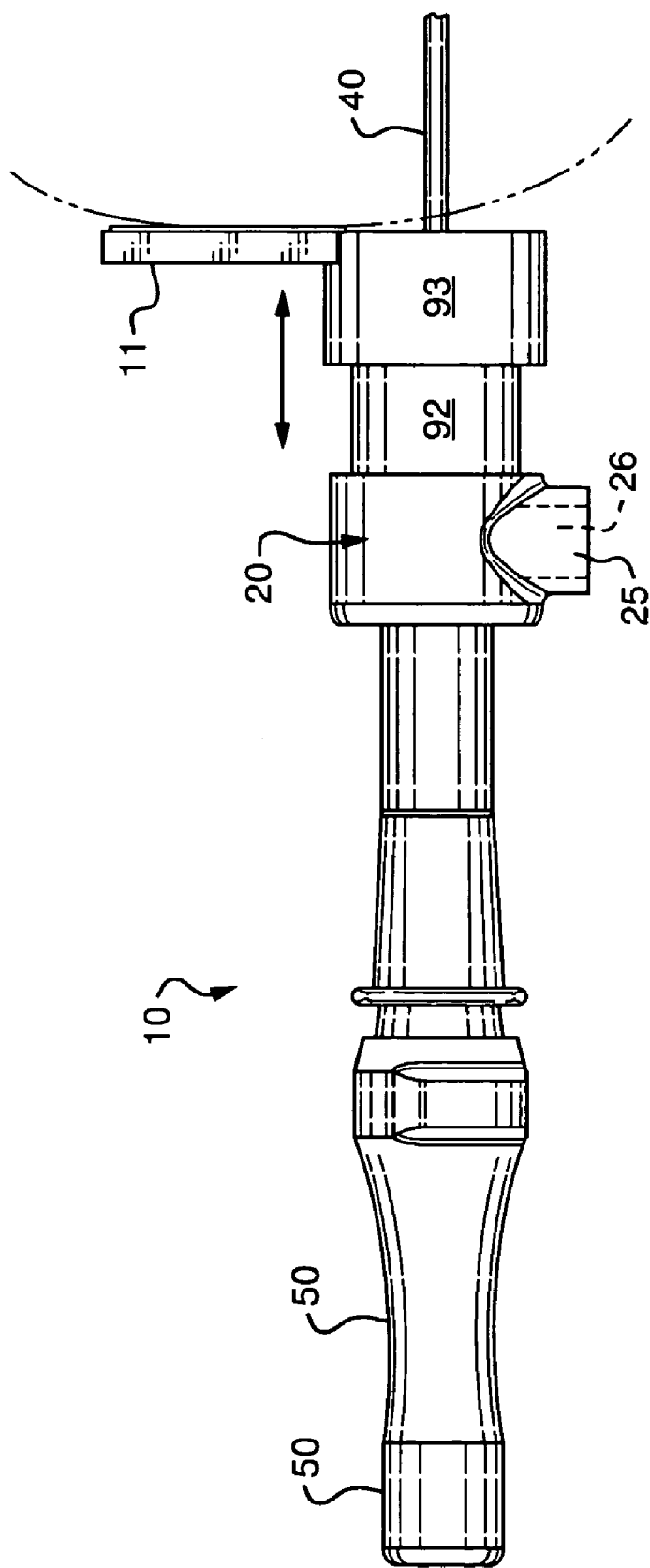
Figure 10:
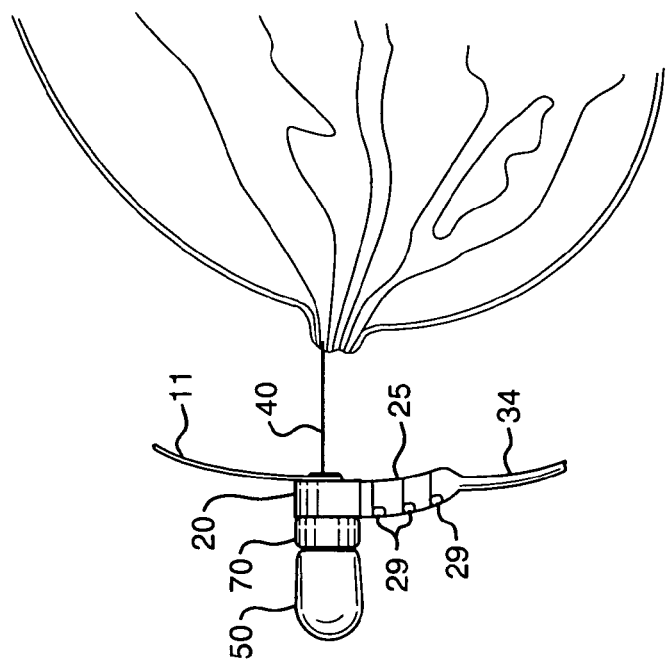
FIGS. 9–11 illustrate a method for introducing the medical instrument of FIG. 1 into a breast duct using a stiff introducer.
Figure 9:
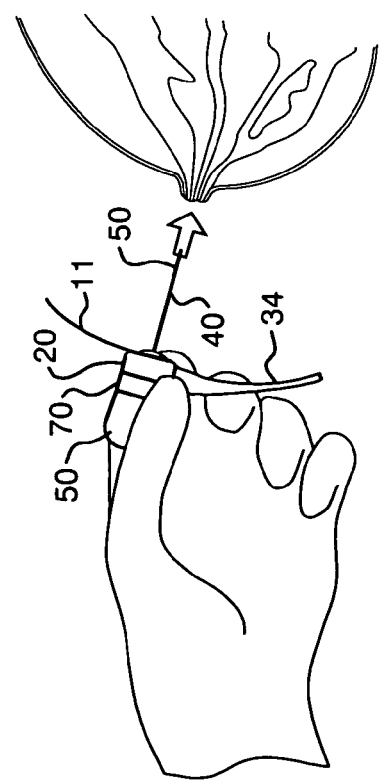

In the event that the manifold hub 20 needs to be spaced from the nipple surface, a retractable spacer 90 may be positioned on the distal end of the manifold hub and at the proximal end of the catheter 40 as shown in FIGS. 7 and 8. The retractable spacer 90 may have a spacing distance in the range from about 1 mm to about 10 mm, most typically in the range of about 5 mm. In a first embodiment, the retractable spacer 90 may include a first spacing member 92 received within a second spacing member 93. Alternatively, the first spacing member 92 may telescopically receive the second spacing member 93. In this embodiment, the first member 92 is secured against movement relative to the manifold hub 20, while the second member 93 is moveable relative to both the first member 92 and the manifold hub 20. In an alternative embodiment, both of the spacing members 92, 93 are moveable relative to the manifold hub 20. The distances required for spacing the manifold hub 20 from the surface of the nipple, for example distances of between about 15 mm and 20 mm, may be controlled by locking the spacing members 92, 93 in an extended position (FIG. 8). Alternatively, the retractable spacer 90 may be locked in a retracted position (FIG. 7). In an alternative embodiment, the retractable spacer 90 includes a single moveable spacing member 95 that slidably receives a portion of the manifold hub 20 to achieve the retracted position and that may be locked at the end of the manifold hub 20 to achieve the extended position. In any of the above-discussed embodiments, the spacing members 92, 93, 95 may be rotated relative to each other and the manifold hub 20 in order to lock each spacing member 92, 93 and 95 against translational movement relative to each other and the manifold hub 20. Any known rotational locking system for telescoping members may be used. Alternatively, the spacing members 92, 93, 95 may be snapped into a locked position using well known snap locks. When additional spacing is needed, members 92, 93, 95 of different sizes or more than two telescoping members may be provided.

The manifold hub 20 may be formed of a transparent material so that an attendant or practitioner may easily view fluid(s) and material(s) within the manifold hub 20. The transparent material may be a plastic, such as ABS plastics or other known plastic materials. As illustrated in FIGS. 1–8, an embodiment of the manifold hub 20 may have a substantially "F" shape.

Figure 2A:
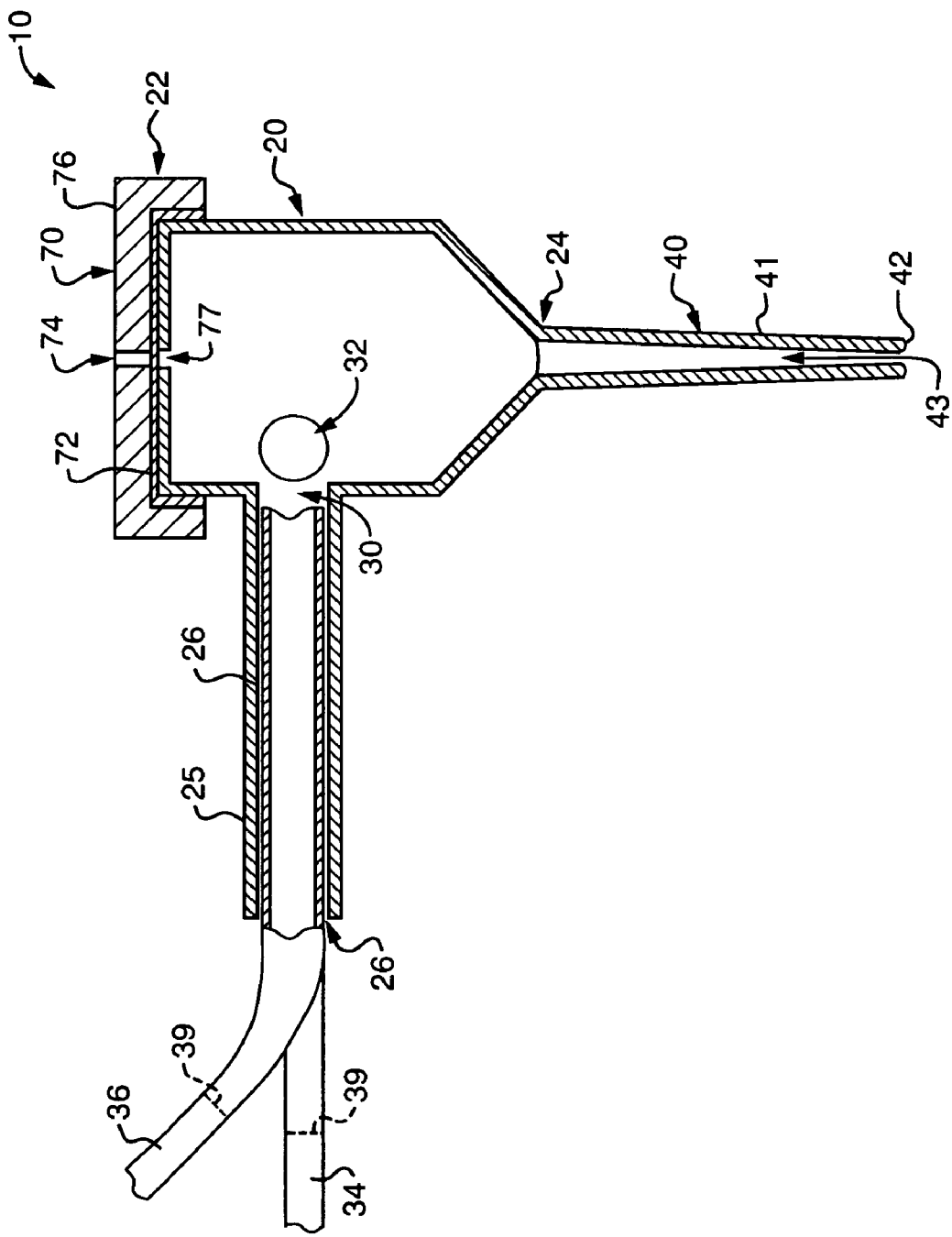
FIGS. 2A and 2B are cross sections of alternative embodiments of the medical instrument illustrated in FIG. 1.
Figure 2B:
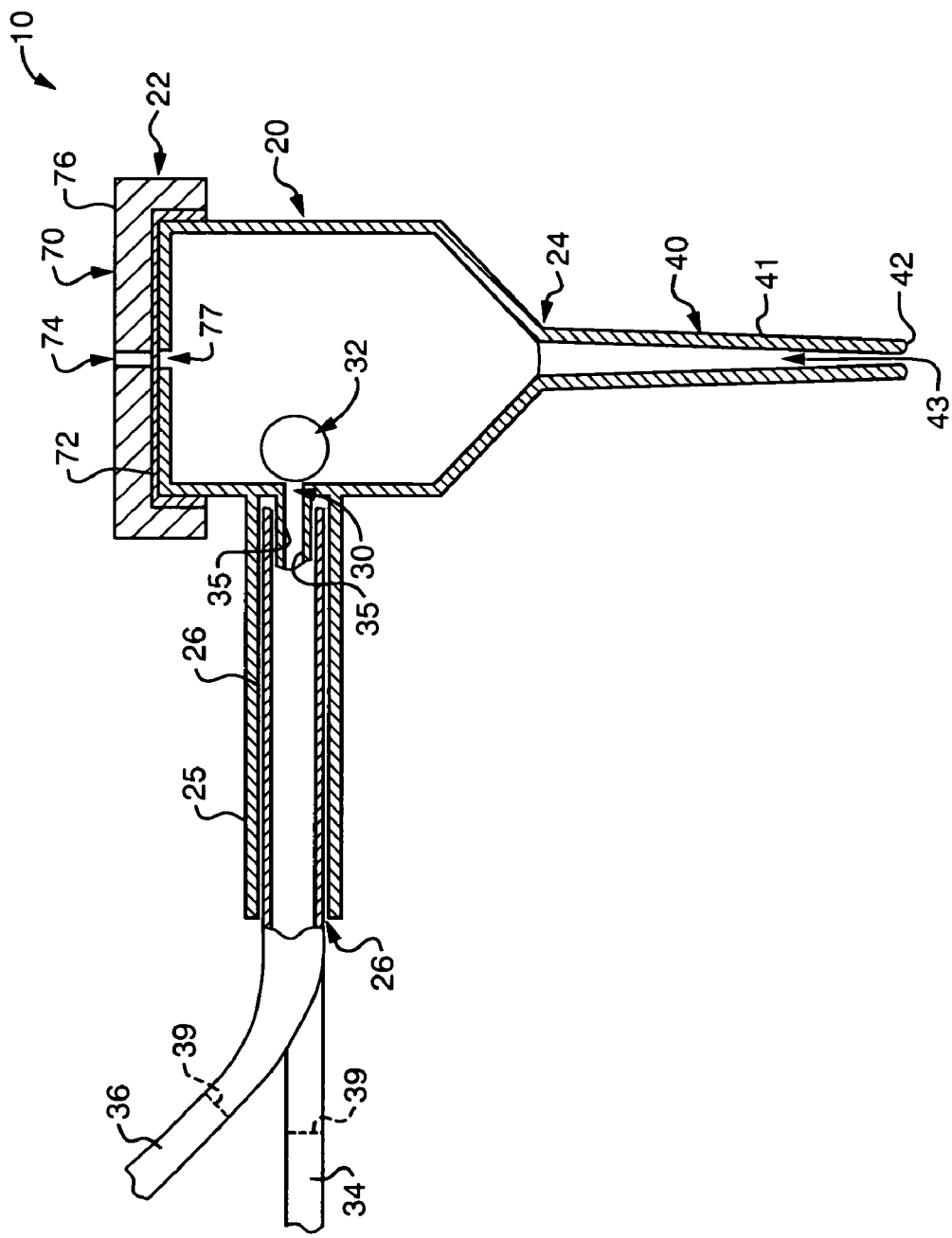
Figure 3:
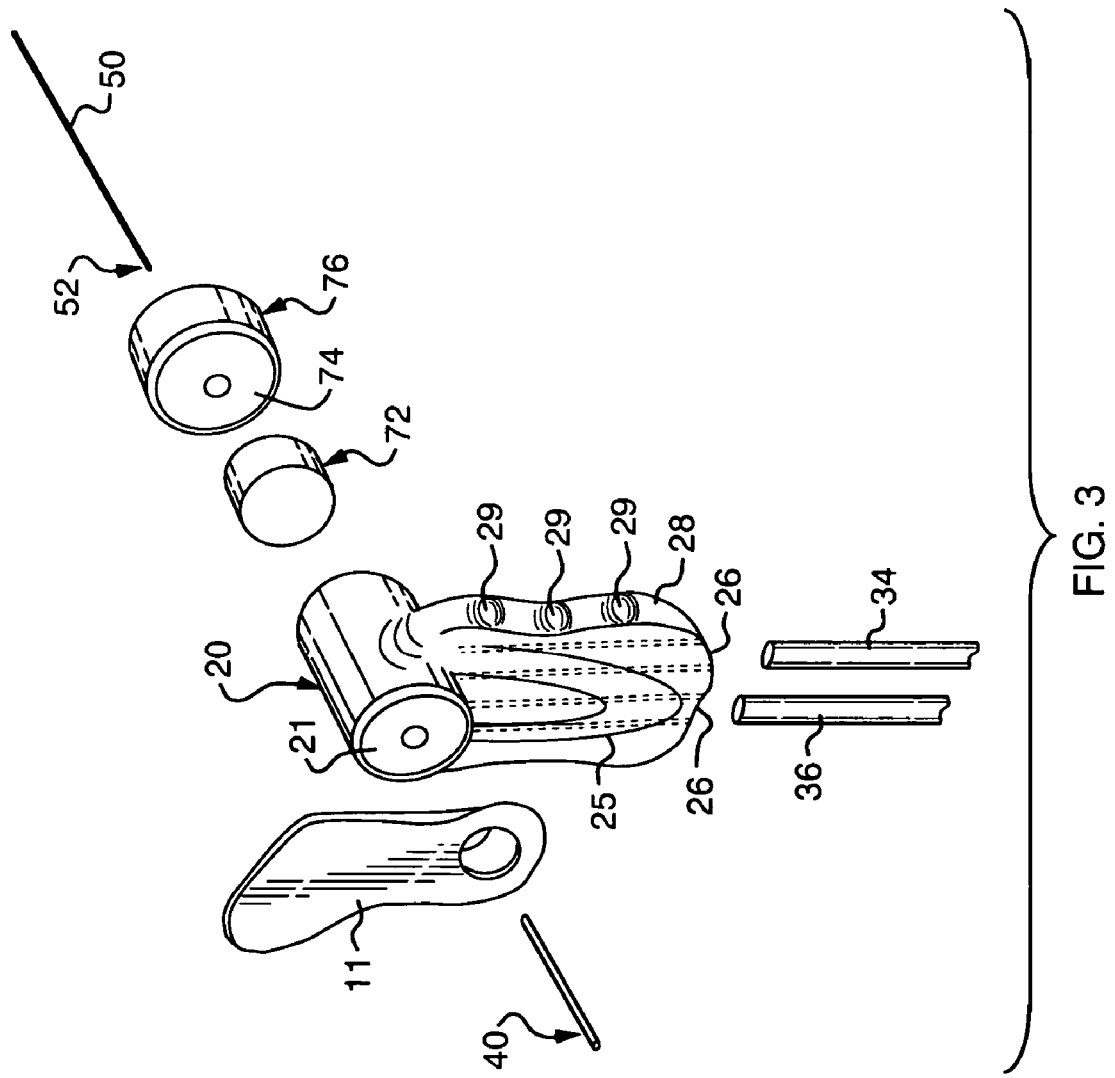
FIG. 3 is an exploded perspective view of the medical instrument of FIG. 1.
Figure 6:
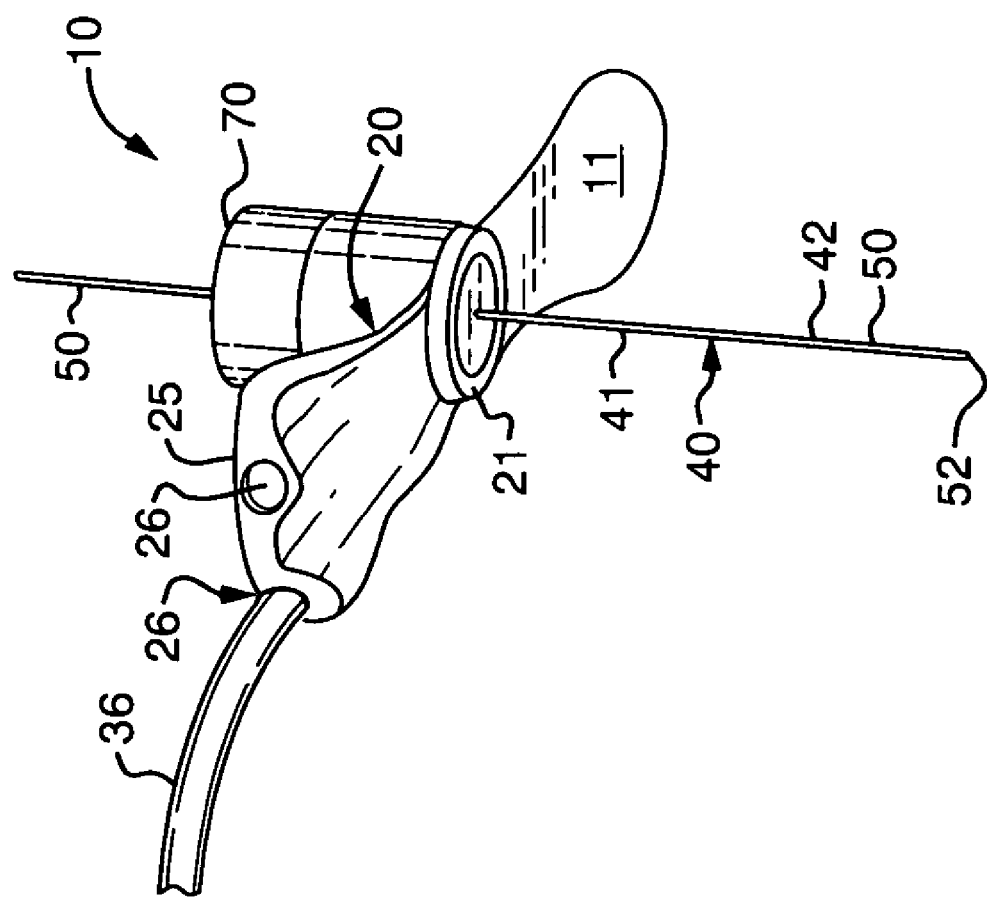
FIG. 6 is another perspective view of the medical instrument illustrated in FIG. 1.

As shown in FIGS. 2A, 2B and 4, the manifold hub 20 includes a first port 30 for connecting to an infusion tube 34 through which materials including wash fluids, diagnostic agents or treatment agents are delivered from an infusion device 38 to the first port 30, the manifold hub 20 and, eventually, the ductal access catheter 40. The connected infusion device 38 may include a syringe or other known fluid containers. In an embodiment, the infusion device 38 may include a fluid receptacle, such as a bag or a container, positioned at a location above the breast of the patient. In this embodiment, the height of the container above the breast of the patient and gravity are used to deliver the fluid from the infusion device 38 to the infusion tube 34.

As shown in FIGS. 2A, 2B and 4, the manifold hub 20 also includes a second port 32 for connection to a collection tube 36. Ductal fluid samples collected from within the breast duct may be delivered from the manifold hub 20 to a collection receptacle 39 via the collection tube 36. The collection receptacle 39 may include a syringe or other known fluid collection device including a medical fluid bag or container. In an embodiment, the collection receptacle 39 may include or be connected to a source of negative pressure so that an area of low pressure may be created within the collection tube 36 and, if needed, the manifold hub 20 for assisting in the delivery of the retrieved ductal fluid sample to the collection receptacle 39. The area of low pressure, for example a vacuum in an embodiment, may be created using a bulb syringe, a hand-operated vacuum source, a foot operated vacuum source or motor controlled vacuum source. These vacuum sources may include a pump that creates negative pressure within the collection tube 36. In addition to a source of lower pressure, or in place of the source of lower pressure, low pressure within collection tube 36 may be created by infusing fluid into the manifold hub 20, thereby increasing the pressure within the manifold hub 20 relative to the collection tube 36. In any of these embodiments, the collection receptacle 39 may be positioned at a location below the patient during the procedure so that the collected ductal fluid sample may be delivered to the receptacle 39 by gravity.

The first and second ports 30, 32 may include an opening along the sidewall of the manifold hub 20 that is round, oval or any other geometric shape conducive to fluid flow either into the duct or out from the duct as shown in FIGS. 2A and 2B. The diameter of the ports 30, 32 may be that diameter which is suitable to achieve a desired flow rate into the duct or aspiration or collection rate out from the duct. Thus, the diameters of the ports 30, 32 may be in a range from about 0.060 inches to about 0.090 inches. One side port 30, 32 may be larger or smaller than the other, especially where such differential port size provides a desired flow rate into or out from one of the lumens, or an overall lavage efficiency of infusion and aspiration or collection of lavage and ductal fluid.

FIGS. 1–6 illustrate that the first and second ports 30, 32 and their associated tubes 34, 36, respectively, are positioned within a connector housing 25 that extends transverse to the longitudinal axis of the manifold hub 20 and the catheter 40. The connector housing 25 may be integrally formed with the manifold hub 20 as a unitary element. Alternatively, the connector housing 25 may be formed separate of the manifold hub 20 and secured to the manifold hub 20 as discussed below with respect to the catheter 40. The connector housing 25 includes two channels 26 that each receives one of the tubes 34, 36. The channels 26 extend from the ports 30, 32 on the manifold hub 20 to the outer, end surface of the connector housing 25. Each channel 26 aligns the received tube 34, 36 with its respective manifold hub port 30, 32 for easy, reliable and quick connection of the tubes 34, 36 to their respective ports 30, 32. The channels 26 also support the tubes 34, 36 at their point of connection to their ports 30, 32 so that the tubes 34, 36 do not create a moment (that may torque the duct) about the point where they connect to their respective ports 30, 32. The connector housing 25 may also include contoured sidewalls 28 with integrally formed, or otherwise secured, ridges 29 that may be gripped by an attendant or a practitioner. The contoured sidewalls 28 permit easy grasping by the attendant or practitioner and allow the attendant or practitioner to orient the instrument 10 during a procedure without looking at the instrument 10.

In an embodiment shown in FIG. 2B, the first and second ports 30, 32 may include posts 35 that extend within connector housing 25 and receive the flexible infusion and collection tubes 34, 36. In an embodiment, the infusion and collection tubes 34, 36 may be formed of flexible tubing such as surgical tubing. However, the tubes 34, 36 may be formed of any flexible material including a flexible plastic. In one embodiment, the tubes 34, 36 are formed of flexible PVC.

The posts 35 may securely receive the tubes 34, 36 when the tubes 34, 36 are positioned over, or within, the posts 35. Alternatively, the ports 30, 32 and their associated posts 35 may include luer lock fittings (not shown) that cooperate with corresponding luer lock fittings on a first end of the tubes 34, 36. The second end of the tubes 34, 36 may also include luer lock fittings that mate with standard luer lock fittings on the syringes or other fluid containers. The luer lock fittings may be either male or female fittings. As discussed herein, the syringes and other fluid containers may carry and infuse saline, diagnostic materials, such as contrast materials, and therapeutic treatment materials into the infusion tube 34. The tubes 34, 36 may be secured to the posts 35 of the manifold hub 20 and the luer locks using a UV curable adhesive or other known bonding agents. In alternative embodiments, the tubes 34, 36 may be secured to the manifold hub 20 and the luer locks by overmolding.

As shown in FIGS. 1–6, the first port 30 may be positioned adjacent the second port 32 along the perimeter of the manifold hub 20. In the illustrated embodiment, the circumferentially adjacent ports 30, 32 are spaced the same longitudinal distance from the first and second ends 22, 24 of the manifold hub 20. This spacing of the ports 30, 32 provides for a compact and low profile manifold hub 20 that, as discussed above, will not create a moment and associated forces that toque the duct when the manifold hub 20 is positioned on the patient and free of support from a practitioner or other attendant.

The second port 32 may be circumferentially spaced any distance from the first port 30 around the wall of the manifold hub 20. In an embodiment, the first port 30 may be between forty-five and ninety degrees offset from the second port 32 around the circumference of the manifold hub 20. In an alternative embodiment, the first port 30 may be circumferentially offset along the manifold wall from the second port 32 by between ninety and one hundred-eighty degrees. In an embodiment, the first port 30 is circumferentially offset from the second port 32 by about one hundred-eighty degrees so that the first and second ports 30, 32 oppose each other within the manifold hub 20.

In an alternative embodiment, it is possible for the second port 32 to be located along the hub 20 at a position that is spaced a greater longitudinal distance away from the catheter 40 than the first port 30. In this embodiment, the second port 32 may be used to collect the fluid that enters the manifold hub 20 from the collection catheter 40. For example one port may be located about 2.0 cm from the distal tip of the catheter 40 and one port may be located about 2.5 cm from the distal tip of the catheter 40.

The tubes 34 and 36 may each include a one-way check valve 39 (FIG. 2A) to control the fluid flow into and out of the manifold hub 20. The check valve 39 in the tube 34 may prevent, for example, wash fluid from flowing back into a syringe connected to tube 34 after being infused into tube 34. Similarly, check valve 39 in tube 36 may be used to prevent retrieved ductal fluid samples in tube 36 from flowing back into the manifold hub 20. In an alternative embodiment, pinch clamps on the tubes 34, 36, may replace one or both of the check valves 39. For example, a check valve 39 may be positioned within the infusion tube 34 and a conventional pinch clamp may be positioned on the collection tube 36. Other known devices for controlling the direction and timing of fluid flow within a tube 34, 36 may also be used.

As shown in FIGS. 1–6, the catheter 40 includes a thin walled microcatheter 41 that is secured to the manifold hub 20. In a first embodiment, the microcatheter 41 is integrally formed as part of the manifold hub 20. In another embodiment, the microcatheter 41 is formed as a separate piece and then secured to the manifold hub 20 by microwelding or a UV curable adhesive. Other known techniques for securing the microcatheter 41 to the manifold hub 20 could be used. In any of the above-discussed embodiments, the catheter 40 may be coated with a known agent to provide a lubricious coating that allows it to be easily introduced into the breast duct openings. The coating may include a lubricant, a cleaning agent, anesthetic and/or a dilating agent. The microcatheter 41 may be formed of any known biocompatible material such as FEP. The catheter 40 may have an outer diameter in a range from about 0.01 inch (about 0.25 mm) to about 0.05 inch (about 1.25 mm) with an inner lumen 43 having a diameter in the range from about 0.008 inch (about 0.2 mm) to about 0.047 inch (about 1.2 mm). In an embodiment, the microcatheter 41 has an inner lumen 43 having an outer diameter of about 0.030 inch (about 0.762 mm) and an inner diameter of about 0.025 inch (about 0.63 mm).

The catheter 40 may include length indicia (not shown) on an outer surface of the catheter 40 that permits a user to determine the depth to which the distal end of the catheter has been introduced into the breast duct. In an alternative embodiment, the catheter 40 could include an integrally formed or attached stop element (not shown) that prevents insertion of the catheter into the duct beyond a predetermined distance. In one embodiment, the stop element may comprise a knob on the catheter 40 having an increased diameter for preventing the distal portion of the catheter 40 from entering a duct a greater distance than the knob is spaced from the distal end of the catheter 40.

As illustrated in FIGS. 1–7, the catheter 40 may be tapered along its length to make a smooth transition with a received introducer 50 so that a perceptible transition between the catheter 40 and the introducer 50 that would cause any pain to the patient is not formed and felt by the patient. The catheter 40 may also include an atraumatic distal tip portion 42 at its distal end. The distal tip portion 42 may be tapered, contoured and/or rounded so as to produce an atraumatic tip that will reduce or eliminate trauma to the duct upon entry through the ductal orifice and introduction into the ductal lumen past the ductal sphincter. The distal tip portion 42 may also reduce or eliminate trauma upon withdrawal of the catheter 40 from the duct after the medical procedure, such as ductal lavage or the infusion of a diagnostic and/or treatment agent, has been completed. The tip portion 42 may be composed of a soft polymeric material, e.g. including polyvinyl chloride, polyethers, polyamides, polyethylenes, polyurethanes, copolymers thereof and the like. The tip portion 42 may have a diameter in the range from about 0.012 inches (about 0.031 mm) to about 0.020 inches (about 0.051 mm). In an embodiment, the tip portion 42 has a diameter in the range from about 0.014 inches (about 0.036 mm) to about 0.018 inches (about 0.046 mm). The length of the tip portion 42 (extending from the distal end of the distal portion of the catheter 40 toward the proximal end of the catheter 40) may be in a range from about 0.10 inch (about 0.25 cm) to about 1.0 inch (about 2.5 cm), more typically in the range from about 0.20 inch (about 0.50 cm) to about 0.70 inch (about 1.8 cm).

The stiffened distal portion of the catheter 40, including the distal tip 42, may have an average bending stiffness in the range from about 0.010 inch-lbs to about 0.5 inch-lbs. The catheter 40 may also have a stiffness that is similar to that of a heavy suture (approximately 0.025 OD). The proximal portion of the catheter 40 may have a cross-sectional geometry and/or size that inhibits insertion through the ductal orifice and into the ductal lumen.

A Touhy-Borst fitting 70 may be positioned at a proximal end 22 of the manifold hub 20 to allow a user to easily receive and move the catheter 40 over an introducer 50 as shown in FIGS. 1–6. The Touhy-Borst fitting 70 is positioned at the end of the manifold hub 20 to cover and seal the opening 77 through which an introducer 50 (discussed-below) including a guidewire, stylet, dilator or the like may extend. The Touhy-Borst fitting 70 comprises a silicone plug 72 including a small aperture 74 for receiving the introducer 50, and a threaded cap 76. When the cap 76 is rotated in a first direction, the silicone plug 72 is altered and the size of the aperture 74 is reduced. This results in the silicone plug 72 forming a seal around the inserted introducer 50. When the cap 76 is turned in a second, opposite direction, the aperture 74 and created seal open, thereby allowing the introducer 50 to be removed. The silicone plug 72 may also be closed to seal the proximal end of the manifold hub 20 so when the introducer 50 is not present so that the distal end of the manifold hub 20 is sealed against fluid flow when the proximal end 22 is free of an introducer 50.

The introducer 50 may be located within the manifold hub 20 to assist in placing the catheter 40 into the breast duct and ductal lumen via the ductal opening as shown in FIG. 1. The introducer 50 may include a tapered dilator, a series of progressively larger diameter dilators, a guidewire, including tapered guidewires, a stylet or other known introducers. As illustrated, the introducer 50 will pass through the Touhy-Borst fitting 70 at the proximal end 22 of the manifold hub 20 so that the introducer 50 may be removed after positioning of the catheter 40 and prior to the infusion/collection of the wash fluid. As discussed above, prior to being inserted into the breast duct, the Touhy-Borst fitting 70 may be turned down over the introducer 50 during introduction and then backed off when the catheter 40 has been positioned within the breast duct to the desired depth. The introducer 50 may be formed of a stiff material such as a metal wire or a flexible plastic cord. In an embodiment, the introducer 50 may be formed of stainless steel or a flexible material such as polypropylene monofilament. In an alternative embodiment, the introducer 50 may be formed of multiple materials or the same materials having different stiffnesses. As a result, the introducer 50 may have sections that are more flexible than adjacent sections of the same introducer 50. As a result, for example, the introducer 50 may have a first, stiff portion for guiding the introducer 50 within the ductal lumen and a second, flexible portion that allows the introducer 50 to conform to the shape of the ductal lumen or lumen branch into which it is introduced. In any of the above-discussed embodiments, the introducer 50 may be coated with a liquid or dry lubricant material that reduces the friction between the introducer 50 and the breast duct during the introduction and advancement of the introducer 50 in the duct.

The introducer 50 may be made of metal or plastics, including shape memory metals and plastics, and may have a tapered and/or an atraumatic tip for gently probing and accessing a breast duct. Preferably, a tapered tip 52 will extend distally of the catheter 40 during the introduction of the catheter 40 into the breast duct. After access of the duct is complete, the introducer 50 may be withdrawn, the Touhy-Borst fitting 70 may be closed and the indwelling catheter 40 may be positioned at a location distal to the ductal sphincter. The introducer 50 may have an outer diameter of from about 0.005 inch to about 0.030 inch. In an embodiment, the introducer 50 has an outer diameter of about 0.010 inch. The introducer 50 may extend through the manifold hub 20 and the lumen of the catheter 40. The introducer 50 may be tapered over its length.

During the process of introducing the catheter 40 into the duct, a ductal opening is located on the surface of a nipple by a practitioner or attendant and a first introducer 50 is advanced through the ductal opening into the duct. The introducer 50 may be a long flexible guide wire, a shorter dilator or any of the other above-mentioned introducers. Prior to, or after the introducer 50 is positioned within the duct, the manifold hub 20 and catheter 40 may receive the first or a second introducer 50. As previously discussed, the Touhy-Borst fitting 70 may be locked about the received introducer 50 to form a fluid tight seal at the distal end of the manifold hub 20 so that fluid does not exit the manifold hub 20 around the introducer 50 during the insertion catheter 40 into the duct (See FIGS. 9, 10, 12 and 13).

Figure 11:
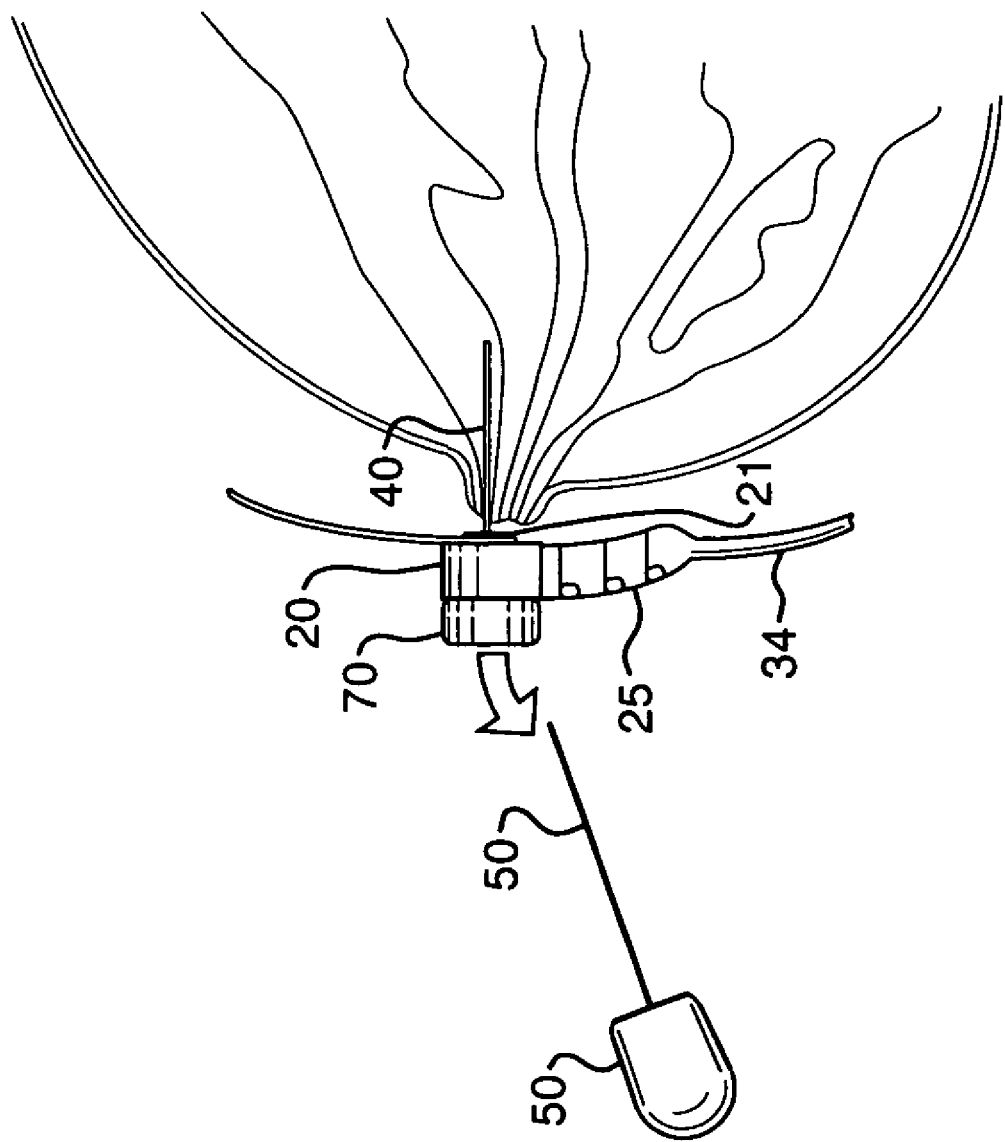
Figure 13:
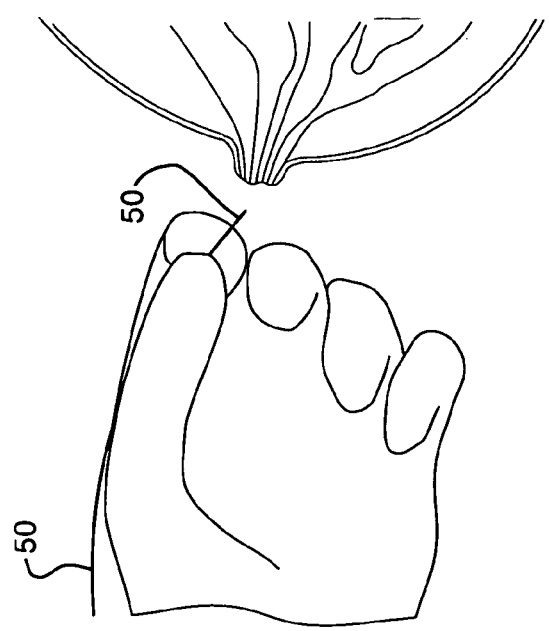
FIGS. 12–13 illustrate an alternative method for introducing the medical instrument of FIG. 1 into a breast duct using a flexible introducer.
Figure 12:
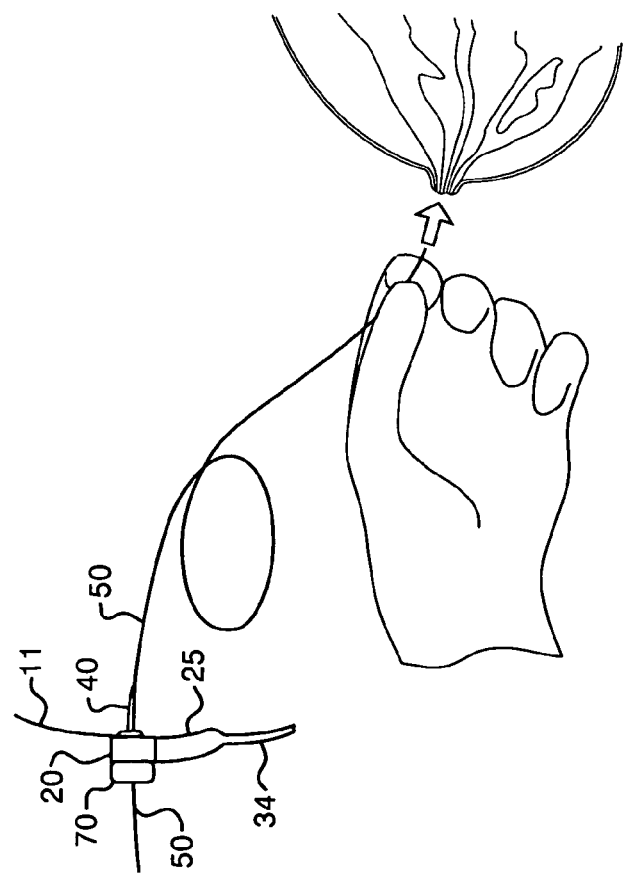

When the catheter 40 is positioned within the duct as intended, the Touhy-Borst fitting 70 is opened and the introducer 50 removed (See FIG. 11). The Touhy-Borst 70 may then be closed again to seal the hub 20. Fluid is then introduced into the manifold hub 20, through the catheter 40 and into the breast duct until resistance is met during the infusion. At this time, it is assumed that the duct is filled. The infusion tube, for example tube 34, may then be closed and the fluid allowed to remain in the duct for a preselected time. During this preselected time, the breast may be massaged and squeezed to stimulate mixing of the wash fluid and ductal fluid, and also ultimately to encourage the fluid to leave the duct and enter the manifold hub 20. The collection tube, for example tube 36, may be opened and the breast squeezed to urge the fluid to progress through the catheter 40 and into the manifold hub 20. If desired, when cloudy return fluid is seen in the hub 20 (which may be transparent or include a transparent window), the infusion tube 34 may be opened and fluid infused into the manifold hub 20 to push the ductal fluid sample that has collected in the hub 20 into the collection tube 36 and a waiting collection receptacle. Alternatively, and possibly additionally, aspiration pressure may be applied within the manifold hub 20 and at the collection tube 36 to aspirate any fluid remaining in the hub 20 into the collection receptacle. The process is repeated either following another infusion of fluid into the duct or by another round of squeezing to encourage return and collection of the infused fluid and cellular material from within the breast duct.

FIGS. 14–17 are schematic diagrams illustrating an alternative construction of a ductal access device. In a preferred embodiment of the invention, the device includes a manifold hub 20 and a ductal access catheter 40 that extends from a distal end 21 of the manifold hub 20 with a centrally disposed single lumen which extends the length of the catheter 40. Catheter 40 includes a tubular introducer pathway adapted to slideably receive a ductal introducer 50 therein. For ease of explanation, as used herein the term "introducer" is defined to include guidewires, dilators, stylettes or portion of any of these that may be inserted within a ductal orifice or a passageway of a catheter sized to access a breast duct.

As illustrated, the manifold hub 20 may have a low profile (height) in a direction that extends parallel to the length of the catheter 40. In another construction, hub 20 has a low profile so as to reduce the torque on the breast nipple after insertion of catheter 40. This overcomes the excessive generated torque on the breast nipple known to cause obstruction of ductal fluid due to compression of the tissue. Thus, improved collection of ductal cellular material is provided.

The manifold hub 20 is coupled to the proximal end 45 of the ductal access catheter 40. In a preferred construction, hub 20 includes transparent material so that the user may visualize the flow to and from the breast duct during a lavage procedure. The transparent material may be plastic, such as ABS plastics or other known plastic materials. As illustrated in FIGS. 14–17, an embodiment of the manifold hub 20 may have a substantially "U" shape.

A fitting 70 may be positioned at a proximal end 22 of the manifold hub 20 to allow a user to easily receive and move the catheter 40 over an introducer 50. The fitting 70 is positioned at the end of the manifold hub 20 to cover and seal the opening 77 through which an introducer 50 including a guidewire, stylet, dilator or the like may extend. The fitting 70 comprises a silicone gasket including a small aperture 74 for receiving the introducer 50, and a cap 76. The cap 76 locks the silicon gasket to the manifold hub 20 thus maintaining a seal between the hub and the gasket. The gasket may be made of any suitable flexible biocompatible material. Around the neck of the silicone gasket are a pair of interlocking hooks 110 which at the terminus of flexible side arms 100 which are part of the main body of the manifold hub 20. Located between the flexible side arms and the manifold hub are one or more springs 120 that force the flexible arms 100 away from the main body of the manifold hub 20. As the springs 120 force the flexible side arms 100 away from the manifold hub 20, the interlocking hooks 110 at the end of the flexible side arms 100 apply pressure to opposite sides of the fitting 70. This results in the fitting 70, which may be comprised of silicone or any other flexible material, to compress around the aperture 74 forming a seal around the inserted introducer 50. When pressure is applied to the flexible arms 100 thus compressing the springs 120, the interlocking hooks 110 are actuated apart thus releasing pressure on the silicon gasket and thus breaking seal around the inserted introducer 50. The flexible side arms 100 and the interlocking hooks 110 may be constructed of metal or plastic or a combination thereof.

In an alternative embodiment, the manifold hub 20 is comprised of a single flexible arm 100 with a single hooked end 110 which, when activated, opens or closes the fitting 70.

Figure 18:
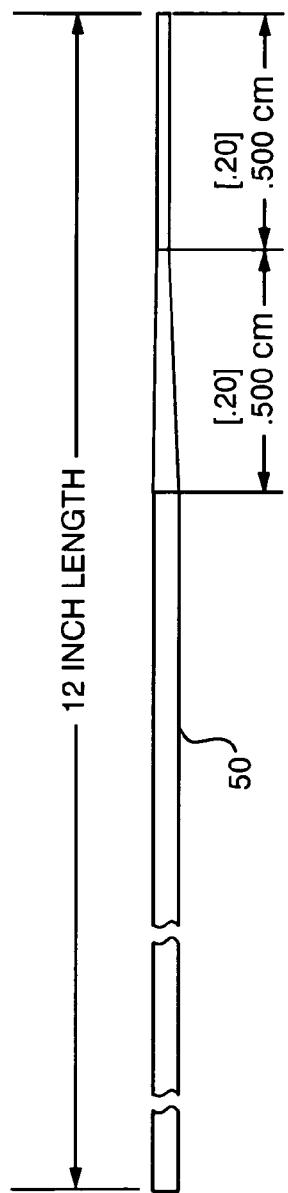

The introducer 50 may be located within the manifold hub 20 to assist in placing the catheter 40 into the breast duct and ductal lumen via the ductal opening as shown in FIGS. 9–13. The introducer 50 may include a tapered dilator, a series of progressively larger diameter dilators, a guidewire, including tapered guidewires, a stylet or other known introducers. As illustrated, the introducer 50 will pass through the fitting 70 at the proximal end 22 of the manifold hub 20. The introducer of the present invention may consist of two parts, a wire and a ring shaped handle located at the end of the introducer. The introducer 50 has a diameter equal to or slightly less than the ID of the catheter 40. The length of the introducer 50 may extend approximately 20–30 mm beyond the distal end of the catheter 40 when the introducer is fully seated. The extended length of the introducer 50 beyond the distal end of the catheter 40 allows the introducer to be used as a dilator prior to the insertion of the catheter in the breast duct. As illustrated in FIG. 18, the distal end of the introducer 50 may be tapered. The distal tip of the introducer 50 may be tapered to an OD in the range of 0.008 to 0.010 inches from the proximal end of the introducer that may have an OD equal to or slightly less than the ID of the distal end of the catheter 42. The small diameter allows for easier insertion of the introducer into the breast milk duct. The introducer 50 may be formed of a stiff material such as a metal wire or a flexible material such as plastic. In an embodiment of the invention, the introducer 50 may be formed of Nitinol. Nitinol is preferred due to its flexibility, durability, and biocompatibility. The introducer 50 may be constructed from a Nitinol wire that is ground to include a tapered small diameter tip. In an alternative embodiment, the introducer 50 may be formed of multiple materials or the same materials having different stiffnesses. As a result, the introducer 50 may have sections that are more flexible than adjacent sections of the same introducer 50. As a result, for example, the introducer 50 may have a first, stiff portion for guiding the introducer 50 within the ductal lumen and a second, flexible portion that allows the introducer 50 to conform to the shape of the ductal lumen or lumen branch into which it is introduced. In any of the above-discussed embodiments, the introducer 50 may be coated with a liquid or dry lubricant material that reduces the friction between the introducer 50 and the breast duct during the introduction and advancement of the introducer 50 in the duct.

The introducer 50 may be made of metal or plastics, including shape memory metals and plastics, and may have a tapered and/or an atraumatic tip for gently probing and accessing a breast duct. Preferably, a tapered tip 52 will extend distally of the catheter 40 during the introduction of the catheter 40 into the breast duct. After access of the duct is complete, the catheter 40 may be slipped over the introducer 50 and positioned at a location distal to the ductal sphincter.

Figure 15:
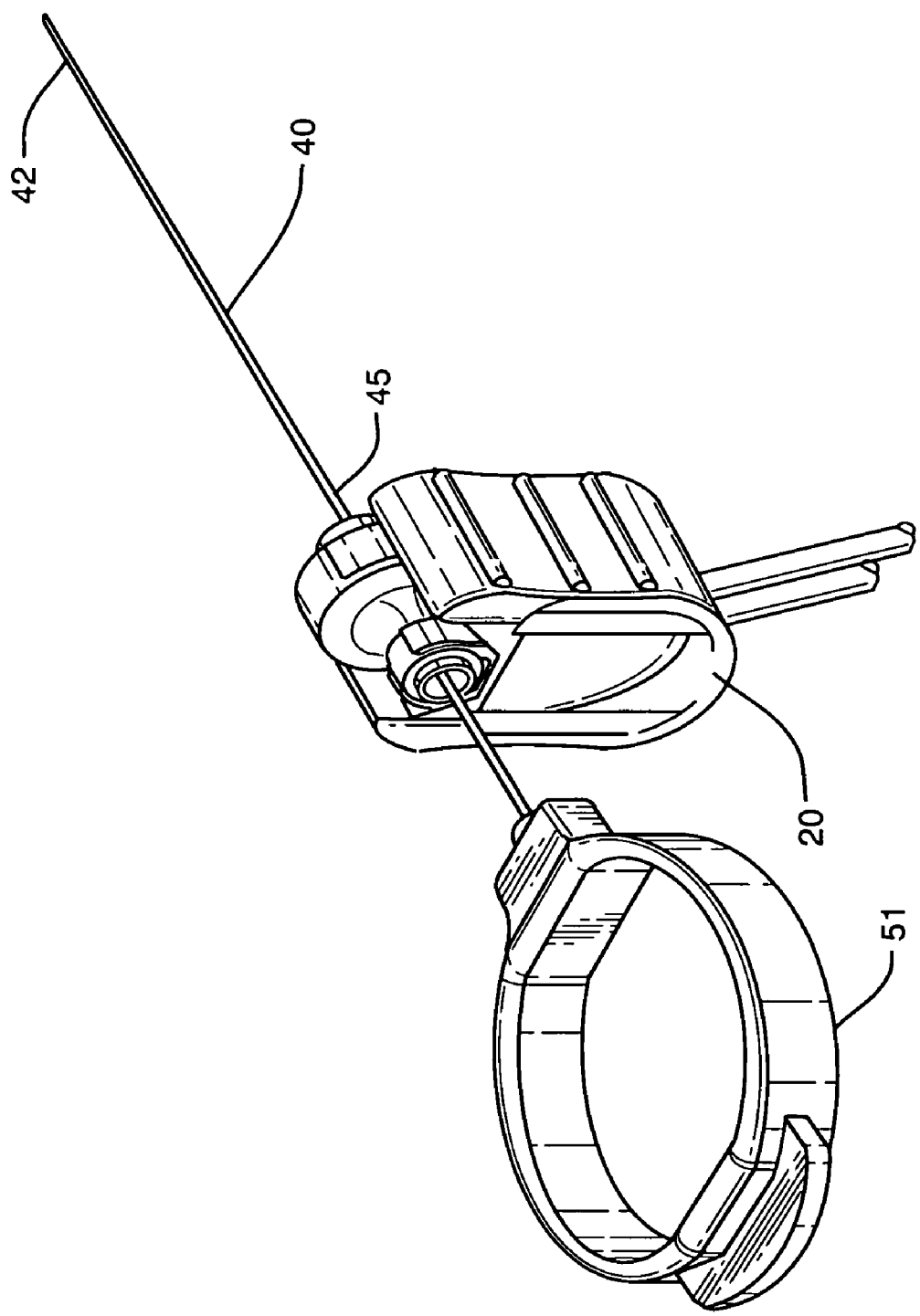
Figure 16:
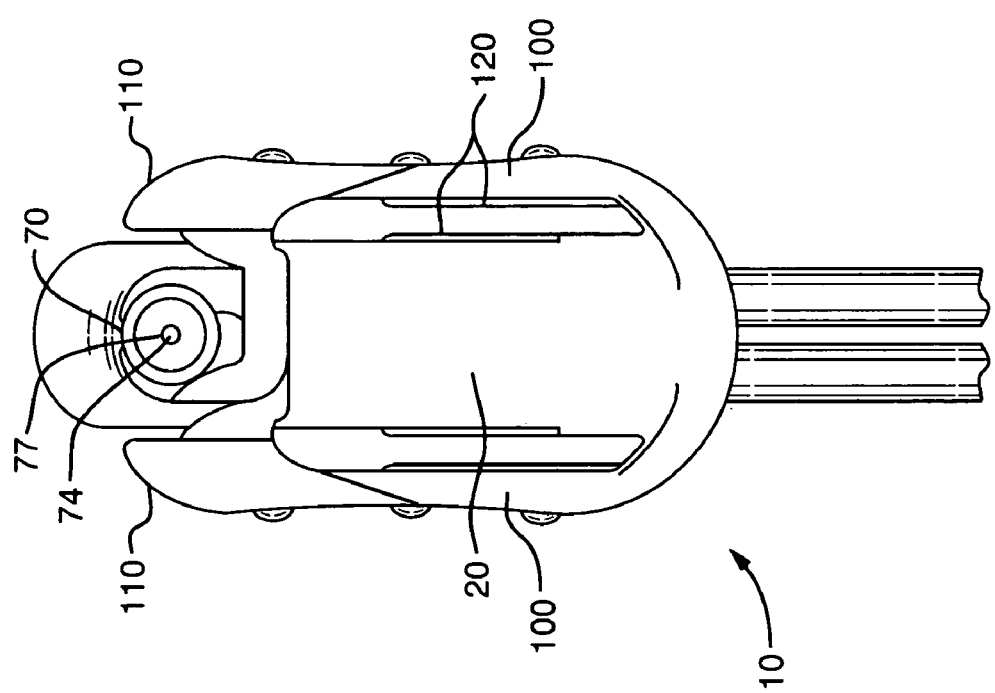
Figure 17A:
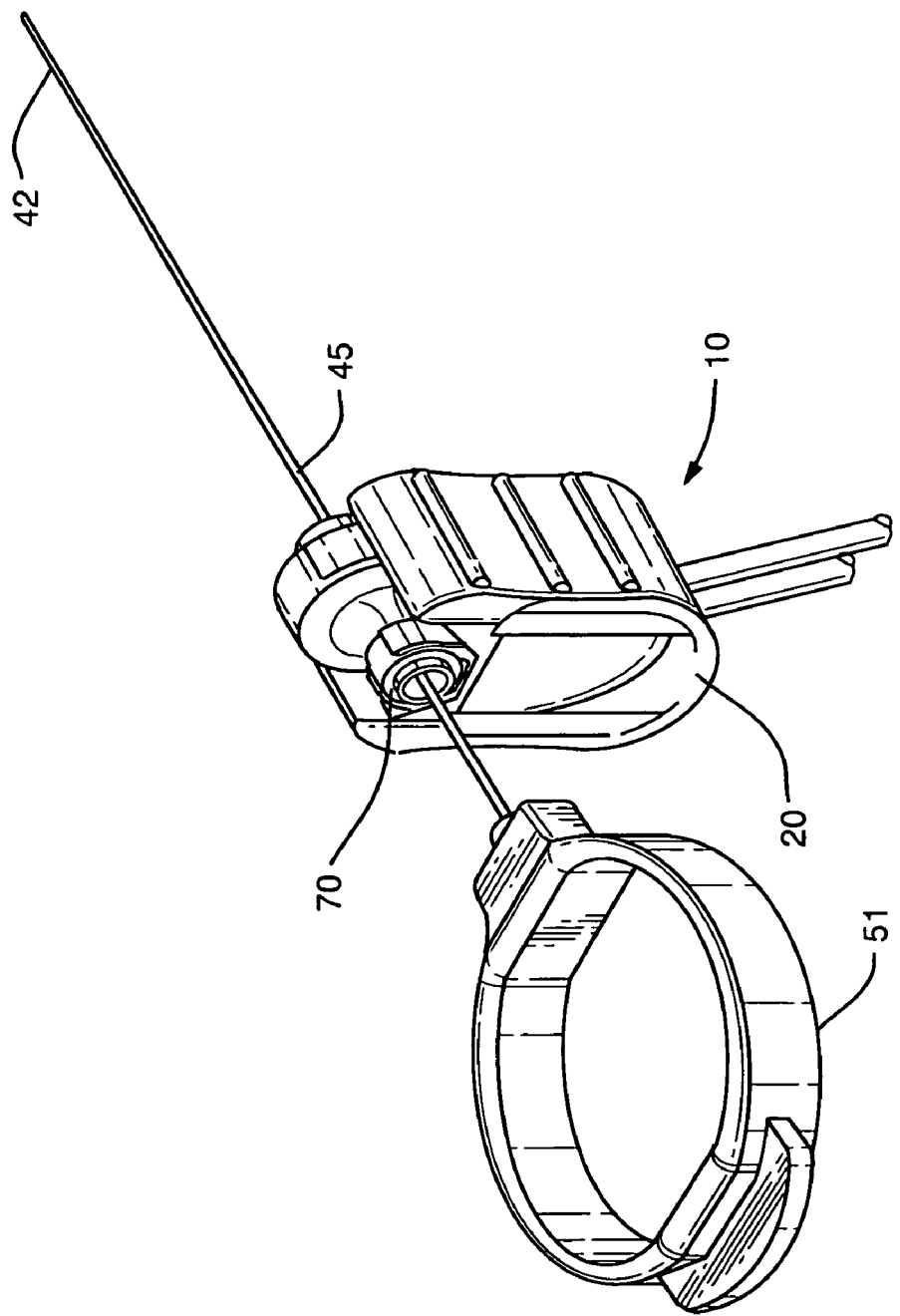
Figure 17B:
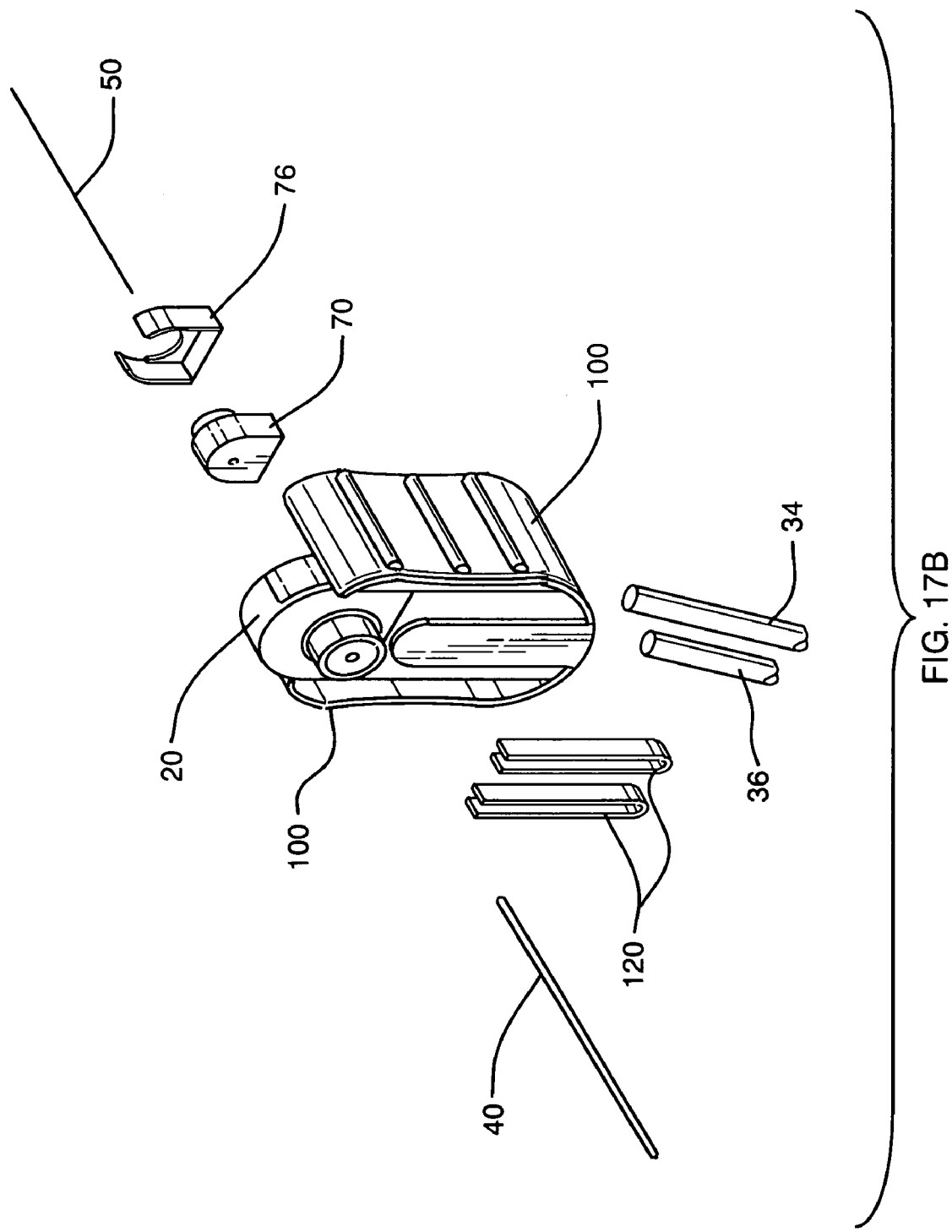

In another embodiment of the invention, the proximal end of the introducer 50 is formed into a ring shaped handle 51 (see FIGS. 14, 15 and 17). The advantage of the ring shaped handle 51 is that is allows the device 10 to be used with one hand. The ring shaped handle 51 may allow the practitioner to grasp the flexible side arms 100 of the device 10 using their thumb and forefinger and to manipulate the introducer 50 by using their index finger which may be positioned through the ring shaped handle 51. The ring shaped handle 51 may be constructed of a thermoplastic such as ABS or polycarbonate or pellathane, and may be shaped in alternative forms that will allow the practitioner to operate the device 10 with one hand.

During the process of introducing the catheter 40 into the duct, a ductal opening is located on the surface of a nipple by a practitioner or attendant and an introducer 50 is advanced through the ductal opening into the duct. The introducer 50 may be a long flexible guide wire, a shorter dilator or any of the other above-mentioned introducers. Prior to, or after the introducer 50 is positioned within the duct, the manifold hub 20 and catheter 40 may receive the introducer 50. As previously discussed, compressing the flexible side arms 100 thus actuating the interlocking side arms 110 away from the fitting 70 may open the fitting 70. Once pressure is released from the flexible side arms 100, the interlocking arms 110 are forced away from the manifold hub 20 by the springs 120 thus closing the aperture 74 about the received introducer 50 to form a fluid tight seal at the distal end of the manifold hub 20 so that fluid does not exit the manifold hub 20 around the introducer 50 during the insertion catheter 40 into the duct (See FIGS. 9, 10, 12, 13, 14, 15, and 16).

When the catheter 40 is positioned within the duct as intended, the fitting 70 is opened and the introducer 50 removed. The 70 may then be closed again to seal the hub 20. Fluid is then introduced into the manifold hub 20, through the catheter 40 and into the breast duct until resistance is met during the infusion. At this time, it is assumed that the duct is filled. The infusion tube, for example tube 34, may then be closed and the fluid allowed to remain in the duct for a preselected time. During this preselected time, the breast may be massaged and squeezed to stimulate mixing of the wash fluid and ductal fluid, and also ultimately to encourage the fluid to leave the duct and enter the manifold hub 20. The collection tube, for example tube 36, may be opened and the breast squeezed to urge the fluid to progress through the catheter 40 and into the manifold hub 20. If desired, when cloudy return fluid is seen in the hub 20 (which may be transparent or include a transparent window), the infusion tube 34 may be opened and fluid infused into the manifold hub 20 to push the ductal fluid sample that has collected in the hub 20 into the collection tube 36 and a waiting collection receptacle. Alternatively, and possibly additionally, aspiration pressure may be applied within the manifold hub 20 and at the collection tube 36 to aspirate any fluid remaining in the hub 20 into the collection receptacle. The process is repeated either following another infusion of fluid into the duct or by another round of squeezing to encourage return and collection of the infused fluid and cellular material from within the breast duct.

In an embodiment, the method of lavage may include seating a patient substantially upright in a chair during the lavage procedure, rather than the standard or classic supine (face up) position. Alternatively, the patient may be ravaged in a prone position, face down, with nipples and breast down. The prone face down position takes advantage of gravity and allows the breast ducts to drain into the collection receptacle during the procedure when the outflow port is open. Thus, as discussed above, the lavaging procedure may include infusing the breast duct with a wash fluid through an open inflow lumen while an outflow lumen is closed; closing the inflow lumen when the duct is filled; squeezing or massaging the breast or both; and opening the outflow lumen to collect the wash fluid.

The cells collected may comprise ductal epithelial cells; the ductal fluid collected may comprise molecular and cellular material. Analysis of the ductal epithelial cells and/or the molecular and cellular material in the ductal fluid may proceed as described below discussing the diagnostic methods possible of these collected materials. The collected cells and fluid and fluid components may be analyzed. The lavage fluid including the ductal cells may be analyzed for diagnostic purposes. Conditions in a breast milk duct that are desirable to diagnose include a cancer or precancer condition. The precancer condition may include atypical ductal hyperplasia (ADH) or low-grade ductal carcinoma in situ (LG-DCIS). The diagnostic agent may also have the ability to diagnose other breast related conditions, including, e.g. fibrotic, cystic or conditions relating to lactation. Diagnostic agents may be mixed with the ductal fluid (either in the lavage procedure, or after the fluid is collected).

The fluid infused into the duct to lavage the duct may include known, biocompatible fluids. These lavage fluids may include saline, phosphate buffered saline, a nonabsorbable fluid, an isotonic solution, an osmotic solution, a hypotonic solution, and a hypertonic solution. The wash fluid may comprise for example, saline, phosphate buffered saline, a nonabsorbable fluid, an isotonic solution, an osmotic solution, a hypotonic solution, a hypertonic solution a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, or albumin.

As mentioned above, a diagnostic or therapeutic agent may be introduced into a breast duct through the manifold hub 20 and catheter 40. The introduced agent for infusing into the duct may comprise a non-absorbable fluid and/or an oncotic agent and/or an osmotic agent. The agent may be soluble. The agent may comprise a molecule that is a protein, a colloid, a sugar, or a polymer. The agent may be mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, or a synthetic colloid. The agent may comprise a protein and the protein may be a binding protein or an antibody. The binding protein may be albumin. Administering may comprise administering locally, and local administration may comprise administering intraductally. A system for increasing or standardizing an amount of fluid collectable from a milk duct of a breast may comprise infusing a nonabsorbable fluid and/or an osmotic agent and/or an oncotic agent into the ductal lumen, a medical tool for delivering the agent to the ductal lumen, and instructions for use.

Any number of alternative combinations could exist for defining the invention, which incorporate one or more elements from the specification, including the description, claims, and drawings, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations.

The invention claimed is:

1. A device for being introduced and positioned within a breast duct for introducing or removing material within the breast duct, said apparatus comprising:
a manifold hub comprising a fitting for sealing about a ductal introducer extending through said manifold hub at one end of said manifold hub said fitting including an aperture that may be repeatedly opened and closed, the sides of said manifold hub comprising two opposing flexible arms connected at one end to the base of said hub and unconnected at the other end and substantially parallel to one another, said arms are held in a sprung position such that said unconnected ends of said arms compress said fitting such that said aperture is closed and when said arms are squeezed together, said unconnected ends of said arms no longer compress said fitting and said aperture is opened.

2. The device of claim 1 wherein said fitting is a silicone gasket.

3. The device of claim 1 wherein springs are located between said flexible arms and the body of said hub such that the springs keep said arms in actuated position.

4. The device of claim 1 wherein the unconnected ends of said arms are interlocking hooks.

5. The device of claim 1 wherein said ductal introducer has a ring shaped handle.

6. The device of claim 1 wherein said ductal introducer is made of Nitinol and has a distal tip that tapers.

7. The device of claim 1 wherein said introducer tapers from approximately 0.025 inches to approximately 0.008 inches.

8. A method for obtaining cellular material from a human breast milk duct using a device comprising a manifold hub comprising a fitting for sealing about a ductal introducer extending through said manifold hub at one end of said manifold hub said fitting including an aperture that may be repeatedly opened and closed, the sides of said manifold hub comprising two opposing flexible arms connected at one end to the base of said hub and unconnected at the other end and substantially parallel to one another, said arms are held in a sprung position such that said unconnected ends of said arms compress said fitting such that said aperture is closed and when said arms are compressed, said unconnected ends of said arms no longer compress said fitting and said aperture is opened; and including the steps of:
inserting the introducer into the internal passageway of a breast duct;
advancing a catheter into the breast duct; and obtaining cellular material.

9. A method for obtaining cellular material from a human breast milk duct using a device comprising a manifold hub comprising a fitting for sealing about a ductal introducer extending through said manifold hub at one end of said manifold hub said fitting including an aperture that may be repeatedly opened and closed, the sides of said manifold hub comprising two opposing flexible arms connected at one end to the base of said hub and unconnected at the other end and substantially parallel to one another, said arms are held in a sprung position such that said unconnected ends of said arms compress said fitting such that said aperture is closed and when said arms are compressed, said unconnected ends of said arms no longer compress said fitting and said aperture is opened; and including the steps of:

- inserting the introducer into the internal passageway of a breast duct;
- advancing a sheath into the breast duct;
- advancing catheter into the breast duct; and obtaining cellular material.

* * * * *